(12) United States Patent
Li et al.

(10) Patent No.: US 10,441,478 B1
(45) Date of Patent: Oct. 15, 2019

(54) HUMIDITY DETECTION DEVICE FOR SMART DIAPER

(71) Applicant: Gallop Creation USA Inc., Milpitas, CA (US)

(72) Inventors: Li Li, Femont, CA (US); Zhigang Wang, Fremont, CA (US); Xu Huang, Zhuhai (CN); Yongqiang Zheng, Zhuhai (CN)

(73) Assignee: Gallop Creation USA Inc., Milpitas, CA (US)

( * ) Notice: Subject to any disclaimer, the term of this patent is extended or adjusted under 35 U.S.C. 154(b) by 61 days.

(21) Appl. No.: 15/963,977

(22) Filed: Apr. 26, 2018

(51) Int. Cl.
| | |
|---|---|
| *A61F 13/00* | (2006.01) |
| *A61F 13/42* | (2006.01) |
| *A61F 13/49* | (2006.01) |
| *G08B 21/20* | (2006.01) |
| *A61F 13/84* | (2006.01) |
| *A61F 13/514* | (2006.01) |

(52) U.S. Cl.
CPC .............. *A61F 13/42* (2013.01); *A61F 13/49* (2013.01); *G08B 21/20* (2013.01); *A61F 13/51478* (2013.01); *A61F 2013/424* (2013.01); *A61F 2013/8479* (2013.01)

(58) Field of Classification Search
CPC .... A61F 13/42; A61F 13/49; A61F 13/51478; A61F 2013/8479; A61F 2013/424
See application file for complete search history.

(56) References Cited

U.S. PATENT DOCUMENTS

| | | | |
|---|---|---|---|
| 9,248,213 B2* | 2/2016 | Gustafson | A61F 13/505 |
| 2004/0147888 A1* | 7/2004 | Huang | A61F 13/42 604/361 |
| 2004/0220538 A1* | 11/2004 | Panopoulos | A61F 13/42 604/361 |
| 2008/0021428 A1* | 1/2008 | Klofta | A61F 13/15 604/385.01 |
| 2013/0135104 A1* | 5/2013 | Nikkanen | G06K 19/07372 340/572.1 |
| 2016/0307430 A1* | 10/2016 | Chen | G08B 6/00 |
| 2017/0354374 A1* | 12/2017 | Pepin | A61B 5/0002 |
| 2018/0253957 A1* | 9/2018 | Jhangiani | G08B 21/20 |

\* cited by examiner

*Primary Examiner* — Francis C Gray
(74) *Attorney, Agent, or Firm* — SV Patent Service

(57) ABSTRACT

A humidity detecting device includes a substrate, a humidity sensor mounted on the substrate, a vent mounted to the humidity sensor, wherein the vent is configured to guide moisture and air from interior of a sample to the humidity sensor, and a spike fixedly coupled to the humidity sensor. The spike can penetrate and hook to the sample, which attaches the humidity sensor to the sample.

10 Claims, 5 Drawing Sheets

HUMIDITY DETECTION DEVICE FOR SMART DIAPER

BACKGROUND OF THE INVENTION

The invention relates to the technical field of wearable devices, and in particular, to a smart diaper having intelligent sensors.

In the conventional technologies, there are often products that need to detect their humidity. Take diaper as an example, especially if the elderly diaper is not wet, the caregiver often needs to check the status of the diaper in order to avoid the user from using the comfort in time.

In order to facilitate the humidity detection, a humidity detection device is generally used to detect the state of the diaper. At present, the humidity detection device has a Velcro patch (HOOK surface). The moisture detecting device is fixed by affixing the Velcro patch to the surface of the diaper. When the diaper needs to be replaced, the Velcro is torn apart and removed from the wet surface of the diaper. The humidity detection device is then fixed on the replaced diaper.

However, the humidity detection device and the diaper are attached only through the Velcro adhesive, and the humidity detection device is located between the Velcro and the diaper. During usage, the diaper twists and moves along with the movement of the user's body, which easily brings outside air between the Velcro and the diaper to reach the humidity sensor in the humidity detection device, which affects the accuracy of the detection. Moreover, the Velcro cannot be affixed to the smooth surface of the diaper. The outside air can easily enter between Velcro and the diaper, the surface of the diaper is not easily moisturized and Velcro can separate from each other, causing the humidity detection device to fall off, which affects the detection accuracy. The attachment between the humidity detection device and the diaper is not reliable.

Instead of a Velcro patch, the moisture detecting device can be fixed by affixing a sticky adhesive to the surface of the diaper. When the diaper needs to be replaced, the adhesive is torn apart for removing the device from the wet surface of the diaper. The humidity detection device is then fixed on the replaced diaper. However, to tear the adhesive from diaper surface might break the diaper surface.

The outside surface of most baby diapers is breathable, and the humidity detection device can detect a wet diaper by just attaching to the diaper outside surface. However, the outside surface of most adult diapers is insulator, and humidity detection device cannot detect the moisture inside the diaper by just attaching to the diaper outside surface.

Therefore, the detection accuracy and the attachment stability have become a problem for humidity detection devices.

SUMMARY OF THE INVENTION

In view of the above, the invention provides a humidity detection device, which improves detection accuracy and attachment stability.

To achieve the above objectives, the present invention provides the following technical solutions:

A humidity detection device includes a detection device and a humidity sensor thereof, further comprising a Velcro patch that includes a window penetrating through the thickness thereof to clear the humidity sensor. The Velcro patch includes a first lamination layer for affixing to the sample to be tested and a second lamination layer for affixing to the humidity sensor. The first lamination layer and the second lamination layer are attached to each other. One side of the first lamination layer away from the second lamination layer includes an adhesive layer for sticking on the sample. The side of the first lamination layer facing the second lamination layer can be a Velcro LOOP surface. The side of the second lamination layer facing the first lamination layer can be a Velcro HOOK surface. In the above humidity detection device, the thickness h1 of the Velcro patch is smaller than the height h2 of the humidity sensor. In the above humidity detection device, the detection device is fixed on a side of the second lamination layer away from the first lamination layer. In the above humidity detection device, a side of the second lamination layer away from the first lamination layer can include an adhesive layer.

In the above humidity detection device, the detection end of the humidity sensor has a spike that can penetrate the sample.

In the humidity detection device described above, the spiking is perpendicular to the axial direction of the humidity sensor.

In the above humidity detection device, the detection end of the humidity sensor has a vent hole, and the vent hole is covered with a filter screen.

The humidity detection device described above further includes a moisture conduit provided on the detection end of the humidity sensor.

In the above humidity detection device, the moisture conduit is disposed perpendicular to the axial direction of the humidity sensor.

In the humidity detection device described above, the moisture conduit has a filter.

In the above humidity detection device, the adhesive layer is a double-sided adhesive layer.

As can be seen from the above technical solution, the humidity detection device provided by the present invention passes through a window and the humidity sensor passes through the window, so that the solid part of the Velcro patch is wrapped around the humidity sensor. The microenvironment of the humidity sensor is isolated from the outside air. The humidity sensor can only detect humidity through its detection end, which improves detection accuracy. The surface of the first lamination layer away from the second lamination layer is directly attached to the sample without being affected by the surface structure of the sample. The restrictions effectively increase the attachment stability between the humidity detection device and the sample.

BRIEF DESCRIPTION OF THE DRAWINGS

To illustrate the technical solutions of the present invention, the accompanying drawings briefly described embodiments need to be used in describing the embodiments. Obviously, the following drawings only describe examples of the present invention. For those skilled in the art, other drawings may also be obtained according to these drawings without any creative work.

DETAILED DESCRIPTION OF THE INVENTION

The invention discloses a humidity detection device, which improves detection accuracy and attachment stability.

The following clearly and completely describes the technical solutions in the embodiments of the present invention with reference to the accompanying drawings in the embodiments of the present invention. Apparently, the described embodiments are merely some but not all of the embodiments of the present invention. Based on the embodiments of the present invention, those of ordinary skill in the art that do not record all the other work under the premise of making the solid obtained in embodiments, are within the scope of protection of the present invention.

Figure 1:
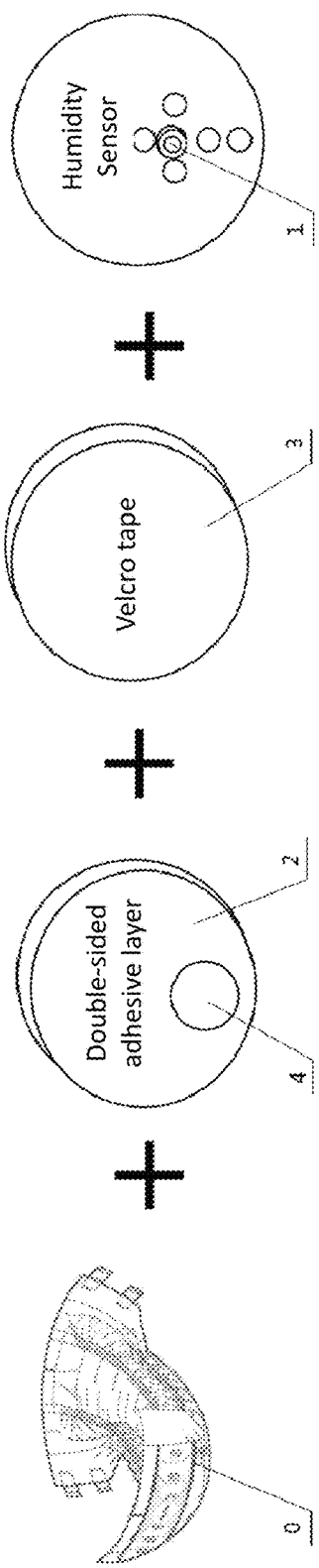
FIG. 1 is a schematic diagram of an exploded view of a humidity detection device according to an embodiment of the present invention.
Figure 2:
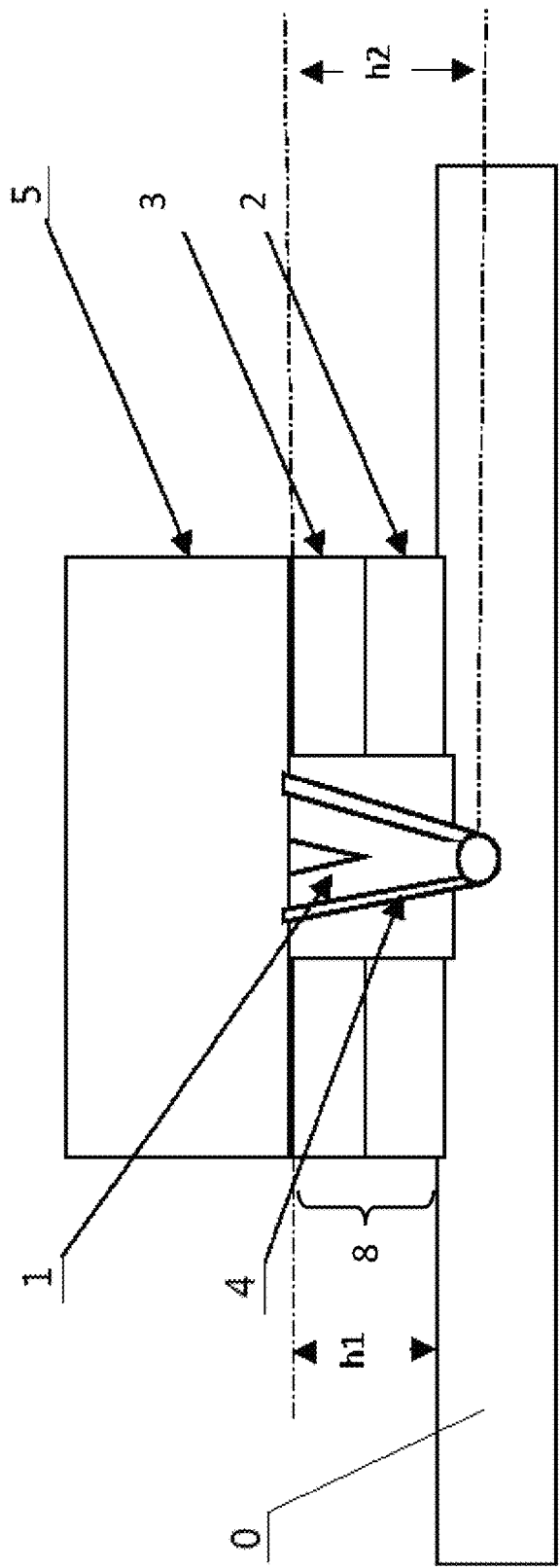
FIG. 2 is a schematic cross-sectional view of the humidity detecting apparatus in FIG. 1.

Referring to FIG. 1 and FIG. 2, in some embodiments, a humidity detection device includes a detection device 5 and a humidity sensor 1 thereof, a Velcro patch 8 comprising a window 4 through its thickness thereof for avoiding the humidity sensor 1. The Velcro patch 8 includes a first lamination layer 2 for affixing to the sample 0 and a second lamination layer 3 for affixing to the humidity sensor 1. The first lamination layer 2 and the second lamination layer 3 are attached together. The side of the first lamination layer 2 away from the second lamination layer 3 includes an adhesive layer for sticking to the sample 0.

Humidity detecting device provides the window 4 and the humidity sensor 1 through the window 4, which allows a substantial portion of Velcro patch 8 to wrap around the humidity sensor 1. Thus the microenvironment of the humidity sensor 1 is separated from the surrounding air; the humidity sensor 1 detects the sample 0 only through the detection end of the humidity sensor 1, which improves the detection accuracy. Moreover, the surface of the first lamination layer 2 away from the second lamination layer 3 is directly attached to the sample 0, and is not limited by the surface structure of the sample 0, which effectively improves the attachment stability between the humidity detection device and the sample 0.

Among them, the sample 0 may be a diaper, such as an infant diaper or an elderly diaper, etc. It may also be other products requiring humidity detection, which are not described here and are all within the scope of protection. In addition, when the humidity detection device is removed from the sample, the first attachment layer 2 can be left on the sample, and the first application layer 2 can be used to re-use the humidity detection device; The first lamination layer 2 is peeled off from the sample, and is affixed to the next sample 0, and the humidity detection device is reused.

The side of the first lamination layer 2 facing the second lamination layer 3 can be a LOOP (round hair) surface. The side of the second lamination layer 3 facing the first lamination layer 2 can be a HOOK (bristle) surface. Since the LOOP surface is relatively soft and the HOOK surface has a relatively high hardness, the above-mentioned arrangement allows the first lamination layer 2 having a relatively soft LOOP surface to be affixed to the inspection sample, thereby improving user comfort.

Of course, one surface of the first lamination layer 2 facing the second lamination layer 3 may be a HOOK (bristle) surface; a surface of the second lamination layer 3 facing the first lamination layer 2 may be a LOOP (rounded) surface.

The thickness h1 of the Velcro patch 8 is less than the height h2 of the humidity sensor 1. Through the above settings, the detection end of the humidity sensor 1 can pass through the Velcro patch 8. After the first lamination layer 2 of the Velcro patch 8 sticks to the sample 0, the detection end of the humidity sensor 1 can enter the inside of the sample 0. In order to detect the humidity of the sample 0. In addition, the humidity sensor 1 can only detect the inside of the sample, further reducing the influence of the outside air on the humidity sensor 1 and improving the detection accuracy.

The detection device 5 is fixed on a side of the second lamination layer 3 away from the first lamination layer 2. Through the above settings, the installation of the humidity detection device relative to the sample 0 is facilitated. Of course, it is also possible to connect the detection device 5 to the humidity sensor 1 via a conductive line in order to keep the detection device 5 away from the Velcro patch 8.

In this embodiment, one side of the second lamination layer 3 away from the first lamination layer 2 includes an adhesive layer. That is, the detection apparatus 5 is stuck on the second lamination layer 3 through an adhesive layer. Of course, the fixing of the detection device 5 can also be accomplished through a snap-fit structure or a screw thread attachment structure, which is described in detail herein.

Figures 3, 4:
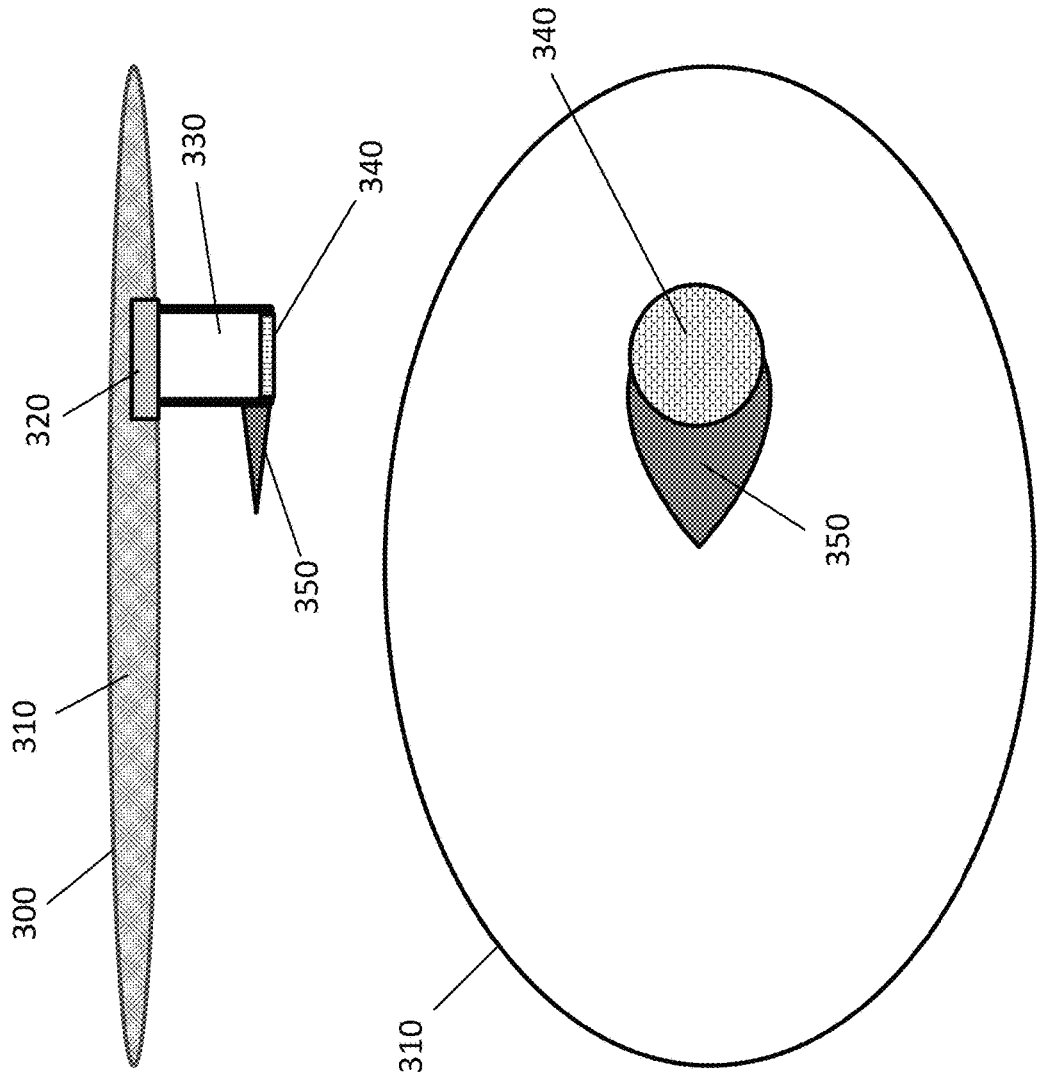
FIG. 3 is a side view of a humidity detection device in accordance with another embodiment of the present invention.
FIG. 4 is a horizontal cross-sectional view of the humidity detection device in FIG. 3.
Figure 5:
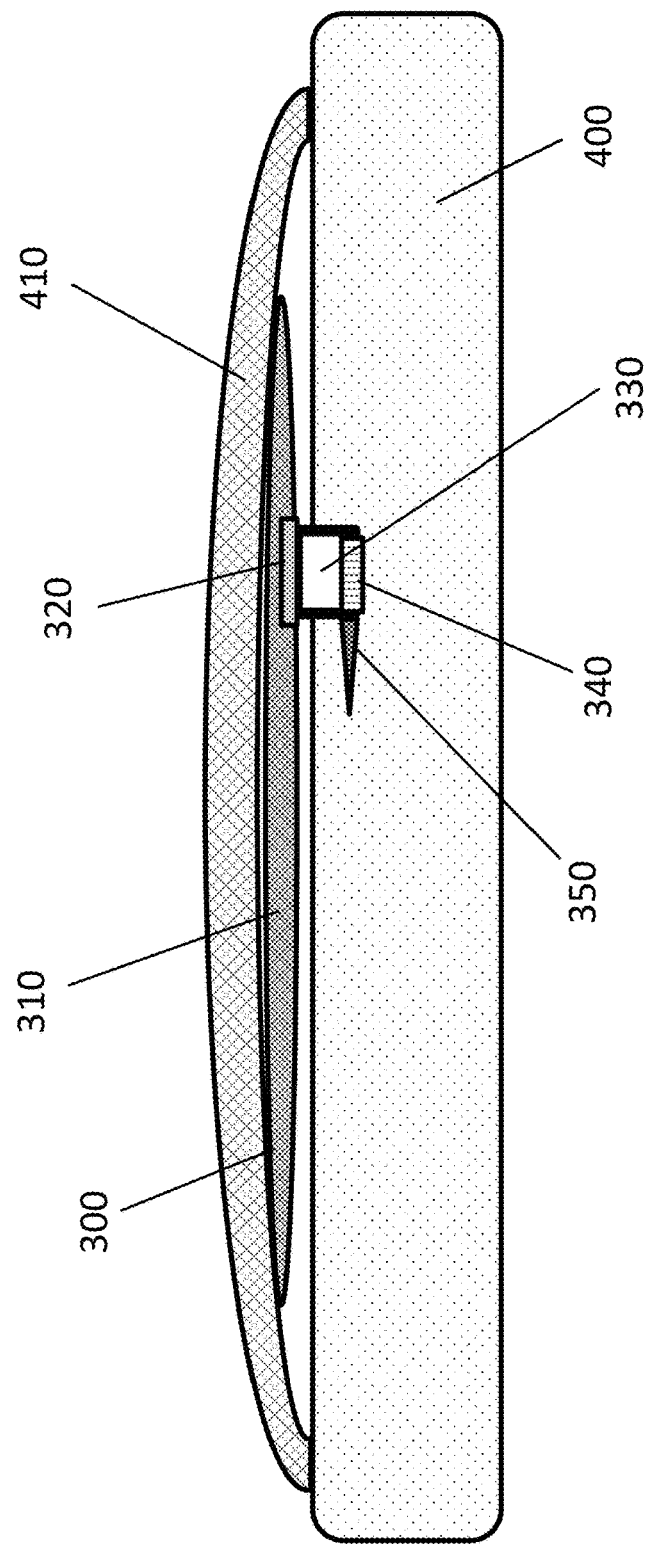
FIG. 5 is a side view of the humidity detection device of FIG. 3 applied to detect humidity of a diaper.

In some embodiments, referring to FIGS. 3-5, a humidity detection device 300 includes a substrate 310, a humidity sensor 320 mounted on the substrate 310, a vent 330 mounted from below to the humidity sensor 320 for guiding air and moisture to be detected to the humidity sensor 320, a screen 340 mounted to cover an entrance of a second end (i.e. detection end) of the vent 330, and a spike 350 mounted on the vent 330. In some embodiments, the spike 350 is fixedly coupled to the humidity sensor 320 in other configurations: for example, the spike 350 can be directly mounted to the humidity sensor 320, or to the substrate 310. The vent 330 defines an axial direction of the humidity sensor 320, which is perpendicular to the substrate 310. The spike 340 is arranged perpendicular to the axial direction of the humidity sensor 320, forming an "L" shaped structure. The spike 350 can penetrate the surface of a sample such as a diaper 400, extends into the interior of the sample. The spike 350 can thus hook the humidity detection device 300 to a sample and keep the humidity sensor mounted 320 attached to the sample. The vent 330 includes a first end attached to the humidity sensor 320, and a detection end that can extend into the interior of the sample (e.g. the diaper 400) to receive moisture and air from inside the sample. The vent 330 can transmit the internal humidity state (moisture and air) of the diaper 400 to the humidity sensor 320, which effectively increases the detection sensitivity of the humidity sensor 320. The screen 340 can be made of a metal mesh, a knitted fabric, or a plastic mesh, which can keep foreign matter from entering the vent hole 330, which may affect the detection performance of the humidity sensor 320. An adhesive layer 410 can cover the humidity detection device 300 to provide protection and attachment to the diaper. The humidity detection device 300 can also include other components such as a temperature sensor, a signal convertor, RF signal transmitter and receiver, a micro controller, etc.

Figure 6:
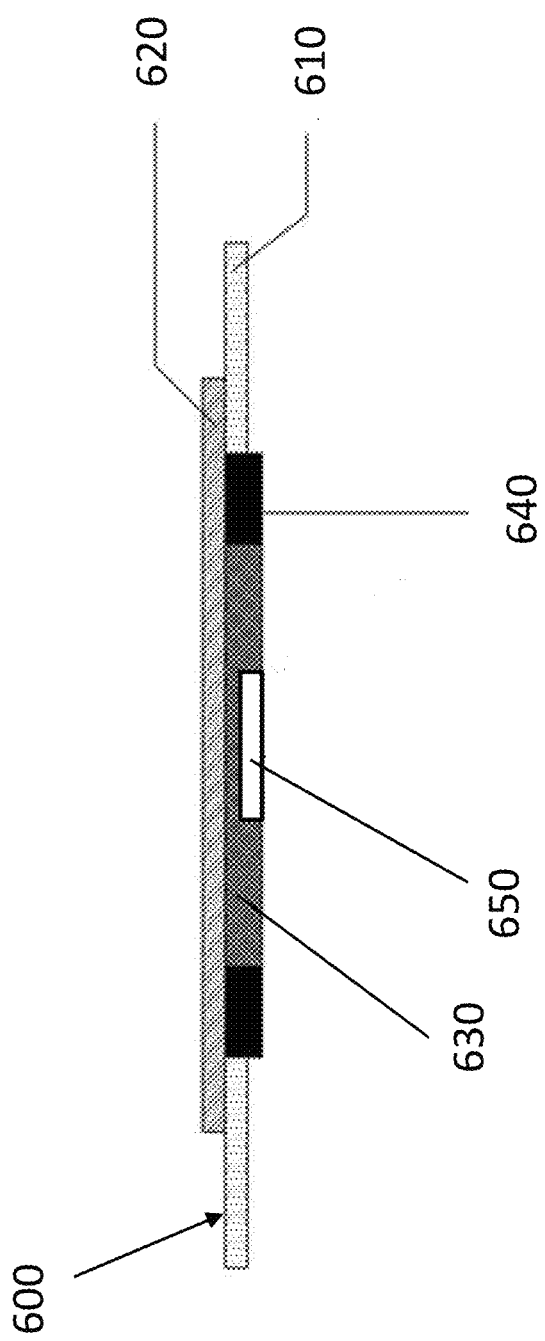
FIG. 6 is a cross-sectional diagram showing a humidity detection device that can be attached to a sample and then removed from the sample without causing damage to the sample in accordance with yet another embodiment of the present invention.

In some embodiments, referring to FIG. 6, a humidity detection device 600 can be attached to a sample such as a diaper to conduct humidity measurement and can subsequently be removed from the sample without causing damage to the sample. The humidity detection device 600 includes a first layer 610 has an opening or a hollow annular structure. The first layer 610 can be formed by a medical non-woven fabric. The lower surface of the first layer 610 is provided with an adhesive layer for bonding with a sample (e.g. a diaper 400 in FIG. 5). In order to prevent the oxidation of the adhesive layer, the surface of the adhesive layer can be covered by a first protective film (not shown in FIG. 6). When the adhesive tape is not wet, the first protective film is peeled off to expose the adhesive layer, and to attach the first layer 610 to the sample by the adhesive layer.

The humidity detection device 600 further includes a second layer 620 with its lower surface adhered to the upper surface of the first layer 610. The second layer 620 can be formed by a medical non-woven fabric. The second layer 620 is positioned over the opening (the hollow area) in the first layer 610. The humidity detection device 600 further includes a leakage-preventing film 630 and a sponge gasket 640 disposed in the hollow area of the first layer 610. The lower surface of the second layer 620 is fixedly connected so that the leakage-preventing film 630 and the sponge gasket 640 to form a similar unitary structure. The humidity detection device 600 includes a humidity sensor 650 mounted to or in the leakage-preventing film 630.

In usage, the first protective film is peeled off to tear off the humidity detection device 600. The adhesive layer on the lower surface of the first layer 610 is adhered to the sample (e.g. the diaper 400 in FIG. 5). When the humidity sensor 650 needs to be removed, the second layer 620 is torn off to detach the second layer 620 as well as the leakage preventing film 630 and the sponge gasket 400 from the first layer 610. The humidity sensor 650 is separated from the sample (e.g. diaper) together with the leakage preventing film 630, without damaging the sample. The first layer 610 remains bonded to the sample.

The above description of the disclosed embodiments enables those skilled in the art to implement or use the present invention. Various modifications to these embodiments will be readily apparent to those skilled in the art, and the general principles defined herein may be applied to other embodiments without departing from the spirit or scope of the invention. Thus, the present invention will not be limited to the embodiments shown herein but will conform to the widest scope consistent with the principles and novel features disclosed herein.

What is claimed is:

1. A humidity detecting device, comprising:
   a substrate;
   a humidity sensor mounted on the substrate;
   a vent mounted to the humidity sensor, wherein the vent is configured to guide moisture and air from interior of a sample to the humidity sensor; and
   a spike fixedly coupled to the humidity sensor, wherein the spike is configured to penetrate and hook to the sample, which attaches the humidity sensor to the sample.

2. The humidity detecting device of claim 1, wherein the vent includes a first end attached to the humidity sensor and a second end configured to receive moisture and air from the interior of the sample.

3. The humidity detecting device of claim 2, wherein the spike is mounted to the second end of the vent.

4. The humidity detecting device of claim 2, further comprising:
   a screen counted at an entrance of the second end of the vent.

5. The humidity detecting device of claim 1, wherein the vent defines an axial direction substantially perpendicular to the substrate.

6. The humidity detecting device of claim 5, wherein the spike is mounted perpendicular to the vent, wherein the spike is perpendicular to the axial direction.

7. The humidity detecting device of claim 1, wherein the spike is configured to attach the humidity sensor to the sample below the substrate, wherein the vent is mounted to a lower surface of the humidity sensor.

8. A humidity detecting device, comprising:
   a first layer comprising an opening and an upper surface and an lower surface;
   a second layer on the upper surface of the first layer, wherein the second layer is positioned over the opening of the first layer;
   a leakage-preventing film fixedly connected to a lower surface of the second layer, wherein the leakage-preventing film is positioned in the opening of the first layer; and
   a humidity sensor mounted to or in the leakage-preventing film, wherein the lower surface of the first layer and a lower surface of the leakage-preventing film are configured to be attached to a sample to allow the humidity sensor to conduct humidity measurement, wherein the leakage-preventing film, the humidity sensor, and the second layer are configured to be detached from the sample and the first layer in a unitary structure after the humidity measurement.

9. The humidity detecting device of claim 8, further comprising:
   a sponge gasket attached to the lower surface of the second layer, wherein the sponge gasket is positioned around the humidity sensor.

10. The humidity detecting device of claim 8, further comprising:
    an adhesive layer on the lower surface of the first layer, wherein the adhesive layer is configured to attached the first layer and the leakage-preventing film to the sample.

\* \* \* \* \*